United States Patent [19]  [11] Patent Number: 4,877,934
Spinello  [45] Date of Patent: Oct. 31, 1989

[54] HYPODERMIC SYRINGE NEEDLE DESTROYING AND STERLIZING APPARATUS AND METHOD

[75] Inventor: Robert P. Spinello, 523 Post Ave., Westbury, N.Y. 11590

[73] Assignee: Robert P. Spinello, Westbury, N.Y.

[21] Appl. No.: 286,321

[22] Filed: Dec. 18, 1988

[51] Int. Cl.⁴ .................. B23K 11/22; B26F 3/06
[52] U.S. Cl. .................................. 219/68; 83/16
[58] Field of Search .............. 219/68, 69 M, 69 R; 110/250; 83/16, 17, 580; 128/303.18

[56] References Cited

U.S. PATENT DOCUMENTS

4,275,628 6/1981 Greenhouse ................... 83/580
4,315,448 2/1982 Ball ............................... 83/580
4,404,881 9/1983 Hanifl ........................... 83/580
4,531,437 7/1985 Szablak et al. ................ 83/580
4,628,169 12/1986 Ching-Lung ................... 219/68

Primary Examiner—A. D. Pellinen
Assistant Examiner—Geoffrey S. Evans
Attorney, Agent, or Firm—Hoffmann & Baron

[57] ABSTRACT

A hypodermic syringe needle destroying apparatus and method using electrical resistance heating between electrodes which are convergent either geometrically or by virtue of relative movement to conduct incinerating currents first throughout the entire length of the contaminated needle and thereafter over progressively shorter lengths until the entire needle is destroyed. Any remaining needle stub can be removed or deformed while in its heated state by impacting it against a deforming barrier.

19 Claims, 6 Drawing Sheets

HYPODERMIC SYRINGE NEEDLE DESTROYING AND STERLIZING APPARATUS AND METHOD

This invention relates to hypodermic syringe needle destroying devices and methods and more particularly to those utilizing electrical resistance heating at the point of use to incinerate and sterilize used needle parts prior to disposal through conventional waste channels.

BACKGROUND OF THE INVENTION AND PRIOR ART

One-time use of hollow hypodermic syringe needles has become the norm in most health facilities because they cannot be reliably sterilized for reuse. The safe disposal of used needles has however, created a problem of its own; the cost to society is enormous and the end results have been less than satisfactory. Bulk incineration of accumulated syringes and needles at the point of use is an obvious but impractical solution because it cannot be accomplished easily, effectively or even safely. And once started toward the dubious but expensive channels of hazardous waste disposal prior to incineration or burial at a central facility the destiny of the syringes with their needles intact or of the needle assemblies per se seems to be all but uncontrollable.

Mechanical shearing devices have long been used at the point of use to sever used needles from their supports. While shearing goes far to prevent reuse of the needle particularly if it is sheared in sections, it is far from a sanitary solution. The severed parts remain sharp as well as contaminated and the shearing operation itself is believed to spread vaporized contamination as part of the shearing impact.

It has been known from the beginning of the electrical age that metallic electrical conductors having a low ratio of volume to surface area, of which a hollow needle is a classic example, will be incinerated when large electric currents are passed through them. A typical modern day device of this type is shown in U.S. Pat. No. 4,628,169 in which portions of the hypodermic needle are successively heated in relatively short sections from the tip inward to achieve incineration temperatures between fixed, spaced apart electrodes while the needle is still attached to the syringe body. No known prior art, point-of-use devices of this type, however, eliminate sharp needle stubs close to the syringe body and none is able to generate heat for a sufficient time to sterilize needle parts much beyond the points of electrode contact. Predetermined or optimized spacing of the fixed electrodes is not a solution to the problem because widely spaced electrodes, in which the spacing approximates the length of the exposed shaft of the needle, leave relatively long sharp stubs of needles attached to the syringe body, for reasons explained below. In addition, the time interval during which current can flow is minimal, with the circuit often being burned open before there is time for heat to be conducted to sections inward of the electrode coupling points to the needle shaft. Close electrode spacing, on the other hand, also restricts the time for the heat to flow along the needle to parts outside of the electrodes, such as those within the syringe body and, in addition, subjects the electrodes to becoming permanently short circuited by fused needle parts to shut down the entire process. And the most minimal practical electrode spacing nevertheless leaves a critical sharp needle stub requiring careful handling to overcome the latent contamination risks.

SUMMARY OF THE INVENTION

The present invention overcomes the several disadvantages found in the prior art designs by providing electrical resistance, point-of-use needle incinerators having unique electrode configurations and associated parts which accommodate a wide range of needle lengths, provide time constants for complete sterilization, positively preclude exposed needle stubs, and which in a variety of species can disinfect needle parts in shielded or recessed portions of disposable or single use syringe bodies.

In a broader concept of the invention two electrodes are provided which are convergent, either geometrically or by virtue of their ability to be relatively moved during the incinerating process from maximum spacing to minimum while the needle remains in its syringe mounting so that the syringe body with its needle can be moved as one as the electrodes converge to destroy successively all parts of the needle shaft and in the process afford time for the generation and conduction of heat back into the syringe body by maintaining electrical contact at the base of needle during the entire cycle. In an embodiment particularly useful with dental syringes in which the needle hub where gripped by the syringe body is metallic and in which the needle is double ended, one electrode comprises an elongated track which is continuously engaged in sliding contact with the hub to conduct electricity into the needle at the point of entry into the syringe body over the full incinerating cycle during which the electrical circuit can open and close randomly as parts of the needle shaft burn away. The other electrode comprises a conducting ramp convergent toward the first electrode track so that the needle is first heated over its entire length and as the syringe is moved laterally to continuously close the circuit burned open by the ongoing incinerating process, all portions are destroyed back to a point adjacent the hub and sterilized even further. An abutment is provided, which if desired can be part of the second electrode itself, over which the incandescent and momentarily softened stub end of the needle is drawn to detach it from the hub. The needle residue is collected in a disposable container below, such residue, however, being sterile and therefore non-hazardous. In embodiments of the invention adapted for use with syringes in which there is no metallic hub carrying the needle, which is typical of those used in the medical profession, the needle stub can be rendered harmless by bending it in its heated malleable condition at the instant it is released from the electrode coupling to fold it back into the then softened thermo-plastic tip of the syringe body. For situations in which a second needle tip is disposed within the syringe body such as double ended needles frequently used in the dental profession, the convergent electrodes can take the form of a pair of relatively movable electrodes preferably spring loaded and having a geometry enabling them to enter confined areas. The normal preactivation positioning of the electrodes should be such in accordance with the invention that they are spaced apart by the maximum needle length intended to be incinerated. As in the case of the fixed, convergent electrode embodiments, the electrodes converge under movement of the syringe to successively destroy the needle from its tip inwardly toward the hub to reestablish the circuit as it is randomly burned open.

DESCRIPTION OF THE PREFERRED EMBODIMENTS

Referring to FIGS. 1–5 an embodiment of the invention is disclosed which is particularly adapted for destroying and sterilizing parts of a used hypodermic syringe S having a hollow needle N attached to a syringe body B (which can be of the autoclavable reusable type or, as is becoming more common, is discarded after a single use). The illustrated syringe needle is a type used in the dental profession; it is double-ended and carried between its ends N-1 and N-2 by a metal hub H gripped by the forward end of the syringe body either in a detachable coupling as when the syringe body is sterilizable for reuse, or permanently molded into an expendable syringe body to be discarded as a unit after one use.

The needle destroying and sterilizing apparatus includes a housing 20 adapted to be self-powered or connected to conventional electrical service mains (not shown) and preferably positioned near the point of use of the syringe by the professional operator. The housing 20 is formed with a deep slot 21 bounded by depending side walls 21a and 21b. The surface of the housing is formed with a slide track 22 defined by lateral guide ribs 22a and 22b to receive the forward end of the syringe body or barrel B and to position the needle N correctly within the housing for carrying out the incinerating process. The housing can include a viewing window with appropriate light filtration to allow monitoring of the incinerating process or alternatively the entire housing can be formed of a semi-transparent material such as smoked plastic.

The housing 20 contains a high current, low voltage power source 23 which can take the form of a rechargeable battery capable of delivering approximately 3 to 6 volts (across the load when the impedance is relatively high) served by a low voltage DC battery charging source through a power cord 24. If desired the power source in the incinerating unit can include its own battery charging circuitry, in which case it can be powered through the cord 24 directly from the AC mains. Alternatively the power source can be a step-down transformer, the primary winding of which is connected to the AC mains by the power cord 24. The DC source or the transformer secondary winding, the latter preferably developing an AC output not greater than 12 volts, is connected across the two electrodes of an electrode array (described below in several embodiments) through a fuse 25 which is preferably a bimetallic, automatic reset fuse via upper and lower contacts 25a and 25b disposed in the housing 20. Currents ranging from 9 to 25 amperes are adequate in most cases to incinerate hollow hypodermic needles of conventional size ranging in size from 18 to 30 gage. The electrode array which engages the needle shafts can be designed for periodic replacement and thus can be incorporated in a disposable box 27 which slides like a drawer in and out of the housing 20. It will be understood, however, one or both of the electrodes can be made a permanent part of the housing 20 or they can be removed from the used box and mounted in a replacement box. When the expendable box 27 is ultimately removed from the housing for disposal with its spent electrodes and a volume of incinerated, sterile needle ash and discrete bits, it can be sealed in accordance with the invention by the cover 31 taken from its duplicate replacement box by reversing the cover lengthwise to bring its interior locking cleats 31a into register with locking cleats 27a on the outside of the box 27. The expendable box 27 is then able to be thrown into conventional channels of waste disposal, free of hazardous contamination.

With the incinerating box in place in the housing and locked in position by a latch 29, with its top removed, the electrode array is centered under the slot 21 and upper and lower electrode contacts 30a and 30b are in engagement with the contacts 26a and 26b, respectively, to energize the electrodes. An on-off switch and pilot light are not illustrated in the drawing but can be provided, if needed.

Figure 5:
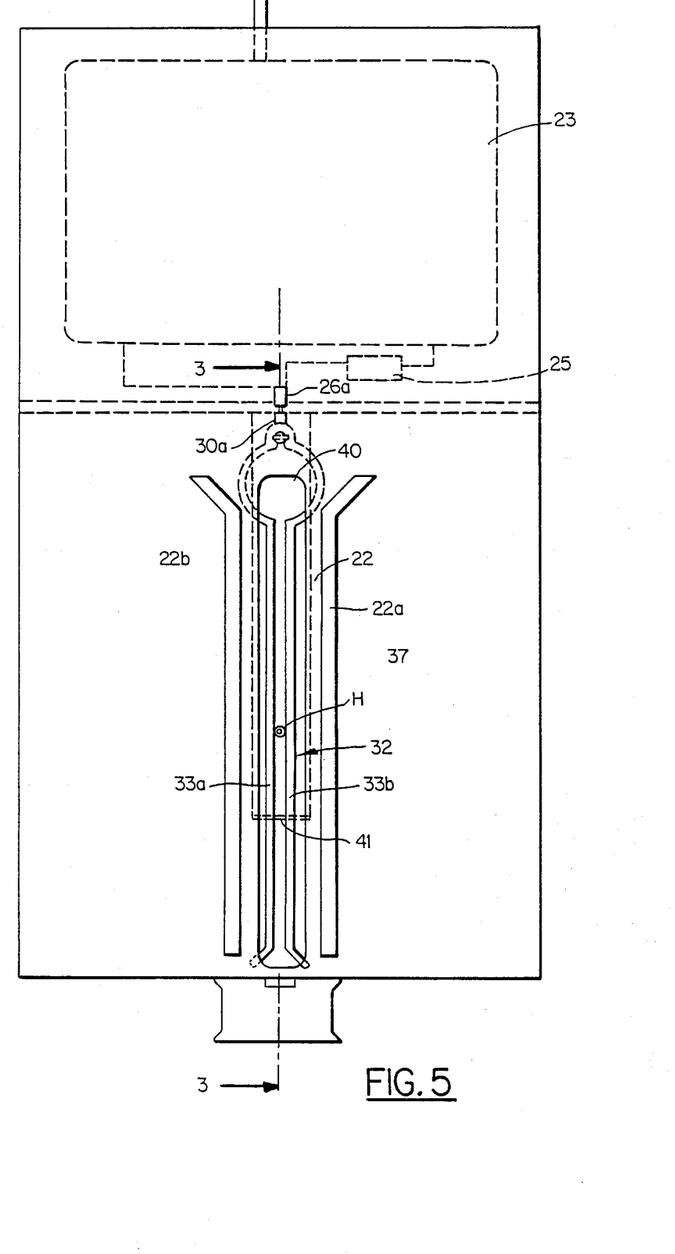
FIG. 5 is a top view of the apparatus shown in FIGS. 1 and 2.
Figure 5A:
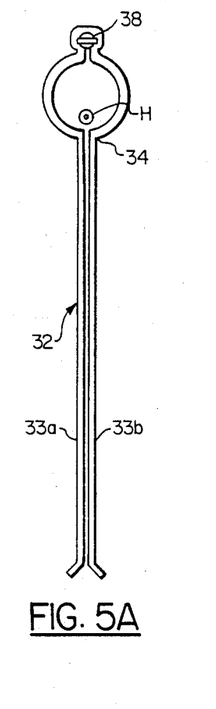
FIG. 5a is a fragmentary view showing the upper electrode removed from the apparatus and in its closed position prior to receiving the needle.

The disposable incinerating box 27 in the illustrated embodiment incorporates the electrode array as renewable elements subject to wear and designed to be discarded after use for, say, one thousand incinerations. The upper electrode 32 forms a track adapted to engage the metallic hub H of the syringe and to conduct electricity to the needle at points closely adjacent the inner end of the needle where it enters the syringe body. The upper electrode as best seen in FIG. 5A can take the form of a number 10 springy wire of electrically conducting material such as copper or aluminum having two elongated parallel arms 33a and 33b normally spring biased together by the action of the circular head 34 which defines an enlarged opening to receive needle N at the entry point at the left hand end of the track as viewed in FIG. 2. The conducting arms 33a and 33b rest in groves 35 and 36 formed in the upper surface of the incinerating box, with the free ends of the arms being splayed outward to center the paired arms directly above the narrow elongated grove 37 in the upper surface of the box. The upper electrode 32 is secured in place by means of a mounting screw 38 which clamps a narrow extension loop 39 to the box body and also secures contact spring 30a which engages the transformer contact 26a.

Figure 1:
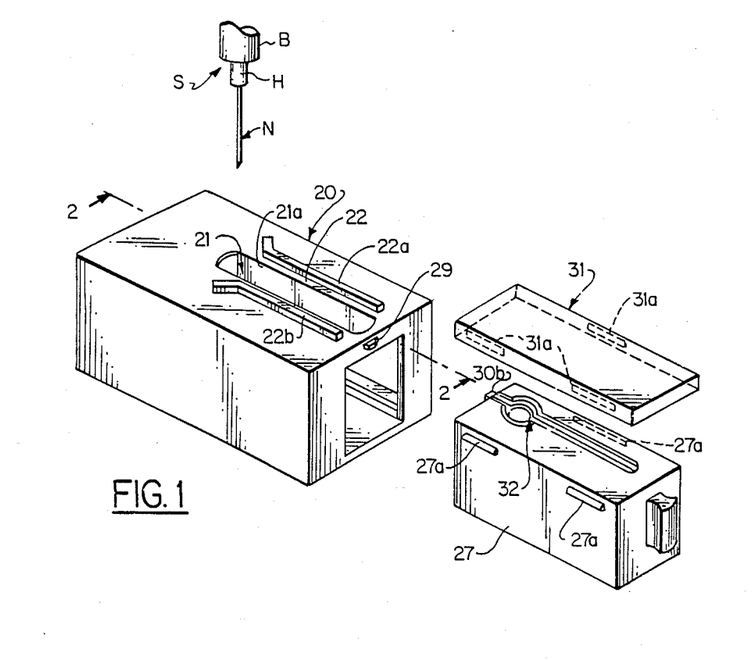
FIG. 1 is a view in perspective of a needle destroying apparatus showing the basic housing part and removed therefrom a disposable and sealable container for sterilized nonhazardous needle ashes and bits, above which is shown a permanent, final cover portion.
Figure 2:
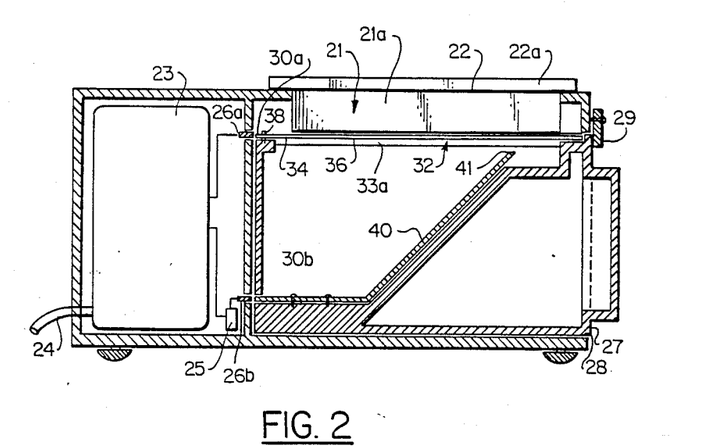
FIG. 2 is a view in vertical section taken on the line 2—2 of FIG. 1 looking in the direction of the arrows and showing the disposable container open and in place within the housing.
Figure 3:
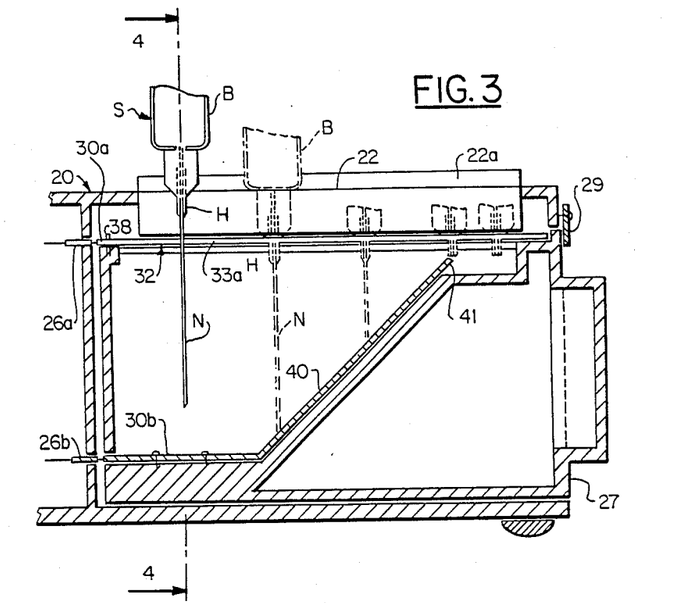
FIG. 3 is a view in vertical section corresponding to the right hand portion of FIG. 2 and as viewed along the line 3—3 of FIG. 5 and showing in progressive steps the position of a hypodermic syringe body and needle in the process of destruction and sterilization.
Figure 4:
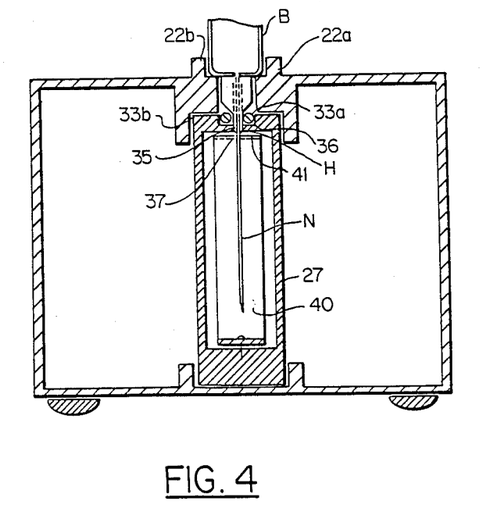
FIG. 4 is a view in transverse section taken on the line 4—4 of FIG. 3 looking in the direction of the arrows.

The electrode array is completed by complementary second electrode 40 which is a metallic conducting plate electrically coupled by the contact 30b to the lower contact 26b. The lower electrode 40 is supported in upwardly convergent relationship with the upper electrode 32. The upper end 41 of the electrode 40 defines a wiping barrier with its uppermost sharp corner which is spaced from the upper electrode 32 by a distance corresponding to the amount by which the hub A extends downward through the upper electrode arms 33a and 33b when the head of the syringe body B is in sliding engagement with the track 22 as best seen in FIGS. 3 and 4. If desired the barrier section 41 can be made more pronounced by forming it at a steeper angle as illustrated by the barrier 41' of FIGS. 6 and 7.

The spacing between the electrodes at the left hand end of the incineration chamber exceeds the length of the longest needle to be accommodated by the unit. As best seen in FIG. 3, with the end of the syringe body B seated on the slide track 22, the needle hub H, when the syringe is moved from the enlarged electrode opening 38, will be engaged laterally by the spring loaded electrode arms 33a and 33b which will be forced apart in their support grooves 35 and 36. When the depending end of the needle N reaches the upwardly convergent electrode 40 current will flow through the needle body from hub to tip, quickly achieving incandescence. The needle will typically burn through at a point between its ends where the cooling effect of the electrodes is least felt, with maximum cooling typically occurring near the hub end due to the relatively large metal masses of the twin electrode arms. The ability of the heated needle to bend will increase the time before the break, if any, occurs to open the circuit, after which further sliding movement of the syringe will quickly reestablish the circuit to resume the heating cycle. By the time the needle reaches the barrier 41 the upper or hub end of the needle will have been heated and reheated over a relatively long time cycle of say 2 to 3 seconds causing heat to be conducted upward into the syringe body to convey sterilizing temperatures into the syringe body beyond the electrode coupling point. Any liquids within the needle will be heated to sterilizing temperatures and driven in a superheated state upward into the syringe barrel.

When the remaining needle stub, heated to incandescence and therefore malleable, engages the barrier 41 it will be detached from the hub H by the wiping action of the hub over the lip of the barrier and will establish a fleeting direct electrical coupling between the hub H and the electrode, generating additional heat. If necessary the hub can be wiped back and forth over the barrier 41 to detach the stub. The physical wiping action will also serve to clear the barrier area of residue. After passing the barrier 41 the syringe body, free of its sharp stub is lifted from the unit. If the syringe is capable of being reused the hub H and internal needle part N-2 can be detached therefrom and further incinerated by the species of the invention described below having reference to FIGS. 8, 8A, B, and C.

Figure 6:
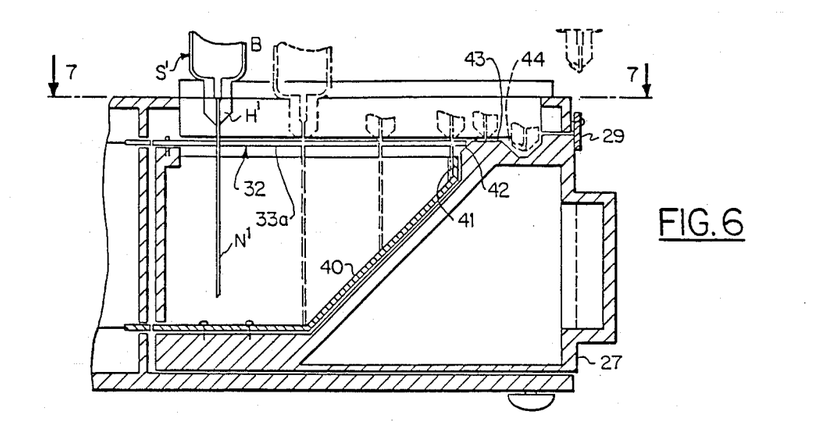
FIG. 6 is a view corresponding to FIG. 5 and as viewed along the line 6—6 of FIG. 7 showing another embodiment of the invention.
Figure 7:
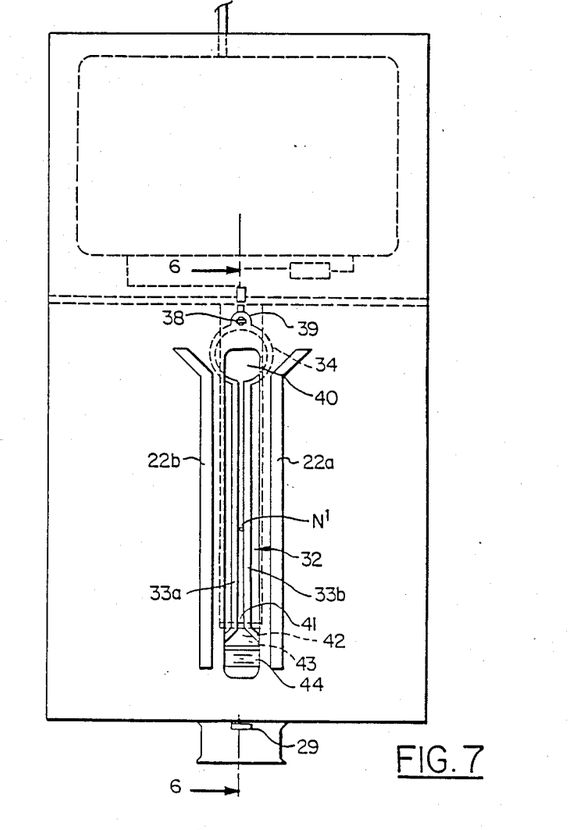
FIG. 7 is a top view of the apparatus of FIG. 6.

Referring to FIGS. 6 and 7 there is illustrated a point-of-use needle incinerating device which is specifically designed to accommodate a type of hypodermic syringe S' widely used in the medical profession in which the hollow needle N' is carried by hub H' formed of plastic and supported by the syringe body B, all of which are intended to be destroyed after a single use. The needle N' is in most cases single ended and is molded directly into the plastic hub H' (without an interposed metallic hub part such as the hub H in FIGS. 1-5A).

The housing and basic electrode parts are substantially identical to those described above having references to FIGS. 1-5A and are identified by like reference numerals with the upper electrode 32 having elongated arms 33a and 33b adapted to be spread apart against the inherent spring action of the head 34 by the thickness of the shaft of the needle N' (as opposed to the greater thickness of the metallic hub H in FIGS. 1-5A). The lower electrode 40 is convergent upwardly toward the upper electrode 32 and can terminate in barrier 41 which is spaced from the upper electrode by a distance which precludes unintended permanent short circuiting by bits of the burned needle becoming fused therebetween. The spacing also defines the length of the needle stub.

Immediately beyond the electrically conducting barrier 41 in the direction of travel of the syringe the housing is formed with an upwardly inclined barrier 42 to a peak 43 followed by a deforming trough 44 of approximately the same width and contour as the lower end of the syringe hub H'.

In operation the Syringe S' is inserted at the left hand end of the track with the needle N' pointing down, until the lower shoulder of the syringe body B' engages the slide track 22. The syringe is then slid to the right as viewed in FIG. 6 until the tip of the needle engages the lower electrode 40 and the shaft of the needle is engaged by the electrode arms 33a and 33b close to the lower end of the hub H'. The electrical circuit is thus completed to heat the entire needle shaft to incandescence and destruction. Thus heated it first bends to enlarge its contact area with the lower electrode and in some cases breaks off as a fully sterilized but deformed section. Meantime the syringe is moving in its track to maintain continuous heating of the needle from the hub downward by electrical resistance heating and from the hub upward into the body of the syringe by conduction. In the process any contained liquids will become vaporized and sterilized. The process continues over a finite time interval of 2 to 3 seconds until all portions of the needle shaft below the level of the top of the electrode barrier 41 are destroyed. A heated shaft stub having a length corresponding to the spacing between the electrode 32 and the top of the barrier 41 remains and is on the order of 2 mm. Immediately, the red hot stub engages the inclined barrier 42 and begins a bending-over process which reaches 90 degrees as the stub passes over the peak section 43, after which it drops into the contoured trough 44 which peens it over. Under the impact with the base of the trough it is pressed into the now softened thermoplastic hub H' to render it harmless as well as sterile. The syringe body which remains can be disposed of by conventional waste disposal means without requiring the use of either hazardous or sharp protection containers. Needle residue, sterile and harmless, is collected in the disposable box 27 which in time due to filling as well as wear of the electrodes will be sealed by a cover 31 as described above and discarded.

If desired the deforming process for the needle stub can take the form of a shearing device or cut off wheel positioned to act on the stub in its heated condition at the instant it leaves the electrodes.

Figures 8, 8A:
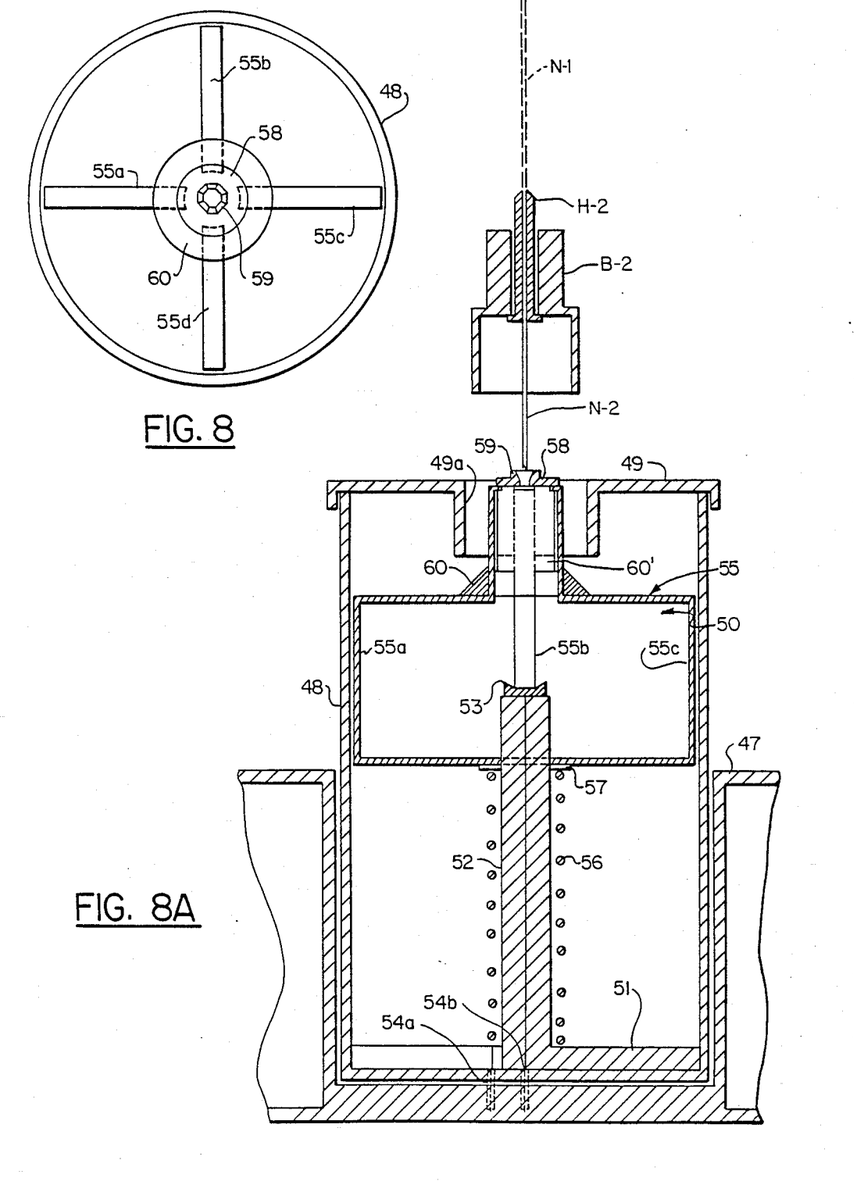
FIG. 8 is a top view with the cover removed of another embodiment of the invention.
FIGS. 8A, 8B and 8C are views in vertical section taken along the line 8—8 of FIG. 8 showing needle destruction in successive stages of operation.

Referring to FIGS. 8, 8A, B and C there is illustrated another embodiment of the invention which is adapted to dispose of a double ended hypodermic needle assembly S-2 including an external sharpened portion N-1 (shown in phantom lines and having previously burned away) and an internal sharpened portion N-2 carried by the central metallic hub H-2 attached to the plastic carrier body B-2. The needle incinerator includes base 47 supporting a disposable outer container 48 having a detachable cover portion 49 within which the permanent electrode array 50 is removably mounted. The electrode array 50 includes a three legged base portion 51 having a pedestal 52 extending upwardly therefrom formed of electrically insulating material and carrying at its upper end cup shaped first electrode 53 connected to one terminal 54a (shown schematically) of a low voltage source (not shown) in the base 47.

The second electrode assembly 55 is adapted to be convergent toward the first electrode 53 by virtue of its ability to be moved axially downward on the pedestal 52 against a compression spring 56 connected at its lower end to a second terminal 54b (also shown schematically) of the low voltage power source. The second electrode assembly 55 comprises a metal cage having four lateral arms 55a, b, c and d attached at their lower ends to a collar 57 surrounding the pedestal 52 and attached to the upper end of the compression spring 56. The cage arms carry an electrode disc 58 having a central contoured electrode ring 59 adapted to be engaged by the metal hub H-2 of the needle assembly. A conical plastic shield 60 and a cylindrical skirt 60' carried by the arms 55a, b, c and d shields the interior of the container 48 at the radial space between the inner wall 49a of the cover 49 and the electrode arms 58.

With the needle carrier body B-2 fitted over the upper cage arms and the electrode disc 58 with the needle N-2 entering the ring 59 it will come to rest with the pointed end of the needle pointed toward the inner electrode 53 and the metallic hub H-2 resting on the upper electrode 59 to establish electrical contact therewith. The carrier body B-2 is then pushed downwardly causing the inner tip of the needle N-2 to engage the inner electrode 53 to establish a flow of current through the needle portion N-2 which will incinerate the needle in the manner described above as the electrodes converge. Suitable stops are provided so that the electrodes 53 and 59 remain out of contact at the extreme end of the incinerating motion as shown in FIG. 8C. The remaining carrier body B-2 can then be removed and discarded. It will be understood that the exposed needle portion N-1 has been previously incinerated by following the same procedure with the needle carrier body reversed. Any needle stubs remaining at the end of the incinerating process can be sheared off by moving the carrier laterally causing the ring electrode 59 to function as a barrier similar to the action of the barriers 41 and 41' described above to shear off the red hot stub. Also, it will be seen that the relatively movable electrodes 53 and 59 in action are convergent and duplicate the functions of the fixed convergent electrodes 31 and 40 of the species of the invention described above having references to FIGS. 1–5A and FIGS. 6 and 7. In all cases the needle is heated throughout the entire cycle from the hub outward to the needle tip allowing time for heat to be conducted to interior parts not spanned by the electrodes and assuring complete heating of all needle shaft parts. Also, the embodiment of the invention shown in FIGS. 8 and 8A, B and C can be used to incinerate the medical needle designs of the type shown in FIGS. 6 and 7.

When the needle parts are incinerated, the ash and pieces of sterilized needle shaft will drop through the cage arms supporting the upper electrode into the cavity within the container 48 surrounding the pedestal 52 and spring 56. After a plurality of incinerations the container 48 can be replaced with a fresh container, capped and discarded after removing the electrode array 50, which is adapted to be installed in the replacement container. Separable electrical contacts (not shown) can be provided for this purpose. Alternatively, the container 48 can be emptied into a non-hazardous waste disposal container and reassembled with the electrode array.

Figure 8B:
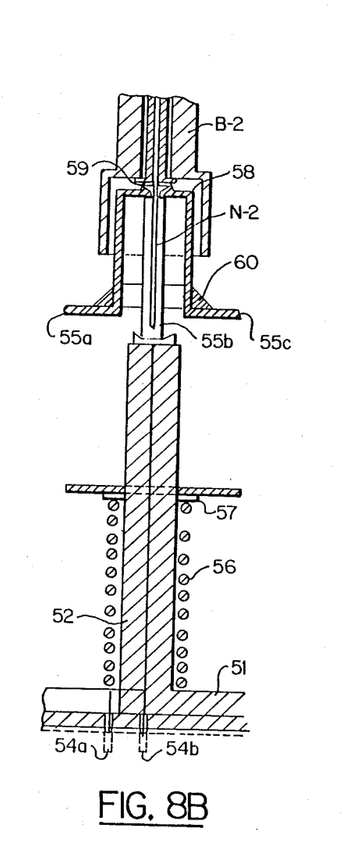
Figure 8C:
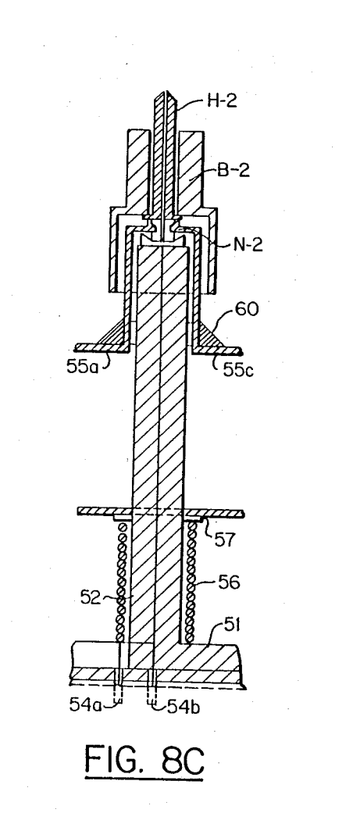

It will be understood that the apparatus of FIGS. 8A-C can be reversed in its mechanical action so that the lower electrode 53 is moved upward toward the upper electrode 59 either by lever action or cocked spring action completed, if desired, by speed control means to establish a relatively slow rate of travel. In such arrangement the syringe body is simply manually held or clamped at the lid with the upper electrode 59 in engagement with the hub H-2, with the lower electrode 53 being supported by a vertically movable carrier to establish convergent electrodes to destroy the needle shaft from the tip inward. As in all embodiments, electrode contact adjacent the hub is continuous throughout the cycle.

Figure 9:
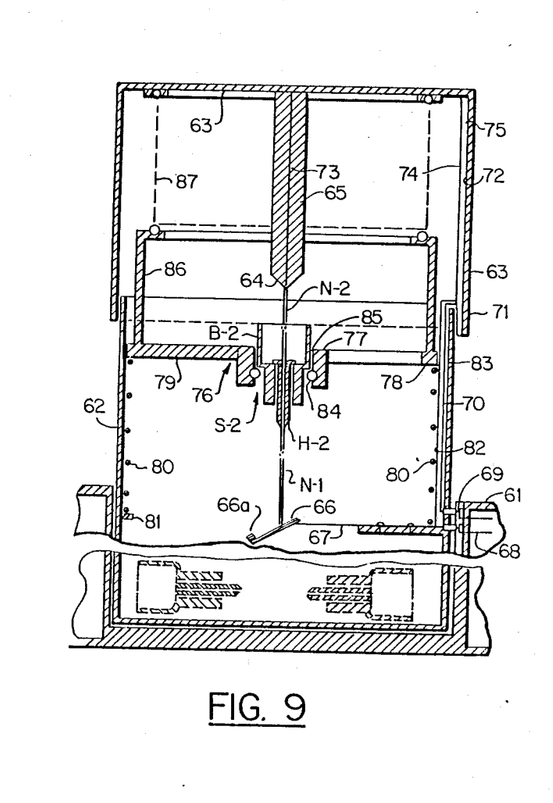
FIG. 9 is a view in vertical section of another embodiment of the invention.

Referring to FIG. 9, there is illustrated another embodiment of the invention which adapted to destroy double-ended needle assemblies S-2 of the type frequently used by the dental profession. A base 61 including a power supply supports a detachable container 62 having a removable cover 63. The cover carries an upper electrode 64 on a support 65 and the container carries the complementary convergent lower electrode 66 on a yielding spring arm 67 connected to an electrical contact 68 (shown schematically) which couples to the power source in the base 61. The upper electrode is energized from an electrical contact 69 through a conductor 70, spring finger contact 71 and conductors 72 and 73. The conductor 72 is bare and seated within a groove 74 in which the spring finger contact 71 rides in sliding contact with the conductor. If desired, the conductor 72 can be covered by an insulator 75 at the upper end of the groove to break the electrical circuit when the cover is lowered to the point of complete needle incineration to open the circuit.

A floating carrier assembly 76 having an inner annulus 77 and an outer annulus 78 joined by radial spokes 79 rides on a light compression spring 80 seated on an abutment 81 and secured against rotation by a vertical rib 82 on the inner wall of the container received in a slot 83 in the outer edge of the annulus 78. The inner annulus 77 is a seat for holding the base B-2 of the needle assembly, which is identical to that described above having reference to FIG. 8A. The body B-2 rests on radially yieldable fingers or alternatively on a yieldable 0-ring 84 and is constrained against rotation by elements 85 which engage the upper side of the body B-2.

Attached to the annulus 78 of the floating carrier 76 is a transparent sleeve 86 forming a finger gripping surface for stabilizing the floating support 76 when the needle assembly S-2 is mounted therein. If desired, an optional upper coil spring 87 can be secured to under-side of the cover 63 to rest releasably on the upper edge of the sleeve 86 to apply balancing forces against the lower coil spring when the cover 63 is lowered, as described below. This force balance relieves the needle part N-2 of most of the bearing load necessary to lower the support 76 and the needle assembly carried thereby into rubbing engagement with the lower electrode 66.

Also, by appropriate selection of springs 80 and 87, the system can be tuned so that the upper and lower electrodes both converge toward the upper and lower ends of the hub at the same time, provided however that the upper spring is stronger than the lower. If for example, needle part N-1 is twice as long as N-2, a spring strength ratio of 2 to 1 favoring the upper will bring the two electrodes to the hub H-2 at the same time. Omitting the upper spring will bring the upper electrode to the hub before substantial movement of the needle assembly occurs, thus delaying complete incineration of the lower needle part and removal of its stub, if any by the barrier 66a.

In operation, when the dentist has finished with the hypodermic injection of a patient, with the cover 63 removed the syringe barrel (not shown) with its detachable needle assembly S-2 is placed vertically into the annulus 77 and the syringe barrel unscrewed from the expendable needle assembly. With the syringe barrel removed, the cover 63 is placed on the container and slowly lowered to bring the upper electrode 64 into contact with the upper needle part N-2 and the lower needle part N-1 into contact with the lower electrode 66. The floating support 76 then moves downward as necessary to establish the current flow through the needle through wiping action on the inclined electrode surfaces.

The needle will immediately be heated to incandescence and will sterilize and destroy itself as the cover is slowly lowered to cause the electrodes 64 and 66 to coverage to points of close proximity to the top and bottom of the hub H-2. This point can be signalled by a releasable detent (not shown). Further smart pressure on the cover 63 will drive the body portion B-2 downward through the yieldable means 84 and in the process will force the lower electrode downward on its spring arm 67 until the body falls into the repository below. Any stub remaining from the needle part N-1 will be broken away by the barrier 66a on the edge of the electrode 66. The momentary dead short across the electrodes by the metal hub H-2 can, if necessary, be overcome either by the circuit breaker or by the insulator 75. As the hub H-2 snaps over the barrier lip 66a on the electrode 67 any stub remaining from the needle N-1 will be removed. It will be understood that the lower end of the container 62 (shown foreshortened in the drawing) is subject to many design variations including, if desired, a removable drawer configuration similar to the drawer 27 in FIG. 1.

While the invention has been illustrated as applied to embodiments found in the field of dental hypodermic syringes it will be understood that the principles of the invention can be adapted to other syringe needle structures having exposed or imperfectly concealed needle portions. Also, additional shielding against the escape of sparks from the relatively small openings can be provided by movable iris vanes or by flexible filaments adapted to yield with the movement of the syringes such shields preferably being disposable with the collection boxes for destroyed needle parts. It will also be understood that dampers can be included to control the rate of syringe motion under hand power or mechanical drives can be used to replace the hand driven motion of the syringe bodies to provide for precision timing of the incineration process. Also, while the lower electrode 40 is shown as being upwardly convergent toward the upper electrode 32, the upper electrode can be contacted downwardly and mounted in a sloping wall part of the housing. The invention should not therefore be regarded as limited except as defined in the following claims.

What is claimed is:

1. Apparatus for destroying and sterilizing hypodermic needle assemblies having a needle shaft, a needle shaft supporting hub and a body portion carrying the hub, comprising, first and second electrodes having a power source connected thereacross, said electrodes having complementary positions spaced apart by a distance corresponding approximately to the full length of the needle shaft to be destroyed, said electrodes being convergent to a point of close proximity, the first electrode being adapted to be electrically connected to the needle shaft at a point closely adjacent one end of the needle shaft, and the second electrode being adapted to engage the needle adjacent the other end to establish a flow of current through substantially the full length of the needle shaft and, as the electrodes converge, to progressively destroy the needle, whereby electrical resistance heating of the needle shaft occurs along the full length of the needle and what remains thereof at substantially all times current is flowing between the electrodes during each destruction cycle.

2. Apparatus as set forth in claim 1 said first and second electrodes being relatively moveable toward each other to a point of minimum spacing.

3. Apparatus as set forth in claim 1 said electrodes being elongated and convergent geometrically whereby the needle shaft when displaced laterally causes the needle shaft to be destroyed in stages successively inward from the tip to the hub.

4. Apparatus as set forth in claim 3 including a housing for said electrodes said housing having an elongated slot parallel and complementary to the first electrode for receiving the needle shaft and hub, and a slide track on the housing to engage the body portion of the needle assembly, said track being spaced from the first electrode by a distance which supports the needle shaft in a position in which the first electrode is electrically coupled to the hub end of the needle shaft, whereby as the body is slid laterally along the track the first electrode maintains electrical contact with the needle shaft adjacent the hub.

5. Apparatus as set forth in claim 4 in which the hub is an electrical conductor and grasps the needle shaft in electrical contact therewith, said slide track being positioned to maintain the first electrode in lateral contact with the hub to establish the said electrical contact with the needle shaft in the interior of the hub.

6. Apparatus as set forth in claim 1, including wiper barrier means to be engaged by the innermost end of the needle at the completion of the destroying cycle.

7. Apparatus as set forth in claim 6 said wiper barrier means being part of the second electrode.

8. Apparatus as set forth in claim 7 adopted for use with needle assemblies in which the hub is metallic, said wiper barrier means being adapted to engage the needle shaft at its point of entry into the hub, said first electrode means being adapted to engage the metallic hub above the point of emergence of the needle shaft.

9. Apparatus as set forth in claim 7 adapted for use with needle assemblies in which the hub is non-metallic, said first electrode being adapted to engage the needle shaft adjacent the point of entry into the hub, said second electrode at its most proximate point to the first electrode being spaced therefrom a predetermined distance to define a needle shaft stub at the conclusion of the electrical resistance heating cycle which has a corresponding predetermined length, whereby the needle stub is heated to incandescence, and means closely adjacent the electrodes to engage and destroy the needle stub.

10. Apparatus as set forth in claim 9 said means to destroy the needle stub comprising stub deforming barrier means closely adjacent the second electrodes to be engaged by the heated needle stub to bend and deform the stub.

11. Apparatus as set forth in claim 4 said housing including a removable expendable inner container to receive destroyed needle parts, at least one of said electrodes being mounted in the inner container.

12. Apparatus as set forth in claim 11 both of said electrodes being mounted in the container and separable electrical contact means carried by the container and adapted to couple to a power source in the housing to energize the electrodes.

13. Apparatus for destroying and sterilizing a double ended needle supported by a body portion which engages the needle between its ends, first and second electrodes adapted to have a power source connected thereacross and respectively adapted to engage the needle ends simultaneously to establish a flow of current through the full length of the needle, said electrodes being convergent to a point of close proximity adjacent the point of support by the body portion, and means to provide relative motion between the electrodes and needle to bring the needle and its supporting body into close proximity with the point of proximate convergence of the electrodes, whereby the needle is destroyed from its ends inward.

14. Apparatus as set forth in claim 13, for use with hypodermic syringes in which the needle assembly is detachable from the syringe, including a support for said body portion of the needle assembly for holding it while the syringe is detached from the needle assembly, said support being movable to comply with relatative movement of the electrodes.

15. Apparatus as set forth in claim 14 including a spring supporting the movable support.

16. Apparatus as set forth in claim 15 including a spring to support the second electrode for yielding movement.

17. A method for destroying and sterilizing used hypodermic needles comprising the steps of causing an electrical current to flow through substantially the full length of the needle shaft from hub to tip in an amount sufficient to heat the needle shaft to incandescence and partial destruction, and thereafter progressively passing current through what remains of the needle shaft from the hub outward until substantially the entire needle shaft is reduced to sterilized bits to a point adjacent the hub.

18. The method according to claim 17 including the step of mechanically detaching any stub portion of the needle shaft remaining at the hub by lateral engagement with an abutment while the stub is in its heated state.

19. The method according to claim 18 including the step of mechanically deforming any stub portion of the needle shaft remaining at the hub while the stub is in its heated state.

* * * * *